(12) United States Patent
Dworschak et al.

(10) Patent No.: US 6,364,887 B1
(45) Date of Patent: Apr. 2, 2002

(54) DEVICE FOR INSERTING A TUBULAR IMPLANT INTO A VESSEL

(75) Inventors: Manfred Dworschak, Duerbheim; Theodor Lutze, Balgheim; Harald Stallforth; Thomas Weik, both of Tuttlingen, all of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/641,470

(22) Filed: Aug. 18, 2000

Related U.S. Application Data

(63) Continuation of application No. PCT/EP99/01073, filed on Feb. 19, 1999.

(30) Foreign Application Priority Data

Feb. 21, 1998 (DE) .......................... 198 07 354

(51) Int. Cl.$^7$ ................................. A61F 11/00
(52) U.S. Cl. ...................... 606/108; 606/198
(58) Field of Search ................ 606/108, 198, 606/192, 194, 1, 105, 106, 107, 139; 623/1.11, 1.2, 1.16, 1.23; 128/831, 843

(56) References Cited

U.S. PATENT DOCUMENTS

| | | |
|---|---|---|
| 4,592,341 A | 6/1986 | Omagari et al. |
| 4,681,110 A | 7/1987 | Wiktor |
| 5,411,507 A | 5/1995 | Heckele |
| 5,443,477 A * | 8/1995 | Marin et al. ................ 606/198 |
| 5,527,355 A | 6/1996 | Ahn |
| 5,713,907 A | 2/1998 | Hogendijk et al. |
| 5,749,918 A * | 5/1998 | Hogendijk et al. ......... 606/108 |

FOREIGN PATENT DOCUMENTS

| | | |
|---|---|---|
| DE | 35 18 238 | 1/1987 |
| EP | 0 605 764 | 7/1994 |
| WO | 95/21593 | 8/1995 |
| WO | 98/09583 | 3/1998 |
| WO | 98/33462 | 8/1998 |

* cited by examiner

Primary Examiner—Kevin Truong
(74) Attorney, Agent, or Firm—Barry R. Lipsitz; Douglas M. McAllister

(57) ABSTRACT

In order to permanently position a tubular implant in a vessel in such a way that it is sealed off in relation to the vessel wall, a device for inserting such an implant is proposed, which is characterized by an introducing head having an advancing handle and being insertable into the implant, with radially outwardly movable spreading elements arranged on the circumference of the introducing head, and by a locking member mounted for displacement on the introducing head and displaceable via a transmission member between a rest position in which the spreading elements are radially retracted and a spread position in which the spreading elements protrude radially outwards.

17 Claims, 2 Drawing Sheets

US 6,364,887 B1

DEVICE FOR INSERTING A TUBULAR IMPLANT INTO A VESSEL

This application is a continuation of international application number PCT/EP99/01073 filed on Feb. 19, 1999.

BACKGROUND OF THE INVENTION

The present invention relates to the subject matter disclosed in international application PCT/EP99/01073 of Feb. 19, 1999, the entire specification of which is incorporated herein by reference.

The invention relates to a device for inserting a tubular implant into a vessel.

Surgical treatment of abdominal or also thoracic aortic aneurysms is usually performed by a large abdominal or thorax incision, with the aneurysmatic vessel portion being clamped out, resected and replaced by a suitable prosthetic section with a manual suture.

Operating methods are also known wherein endoluminally a tubular implant is introduced into a vessel and fixed there, for example, with the aid of barbs (U.S. Pat. No. 5,527,355 A). Such endoluminal techniques are much less stressful than conventional surgical operations, but increased risks are also involved. There is the danger that the tubular implants inserted will shift within the vessel, and, in addition, leakages may occur in the area of the proximal and distal attachments of the tubular implants in the vessel.

The object of the invention is to so design a device for inserting a tubular implant in a vessel that after insertion into the vessel, a tubular implant can be easily and safely fixed on the vessel and sealed off in relation to the vessel with this device.

SUMMARY OF THE INVENTION

This object is accomplished in accordance with the invention by a device for inserting a tubular implant into a vessel, which is characterized by an introducing head having an advancing handle and being insertable into the implant, radially outwardly movable spreading elements being arranged on the circumference of the introducing head, and by a locking member mounted for displacement on the introducing head and being displaceable via a transmission member between a rest position in which the spreading elements are radially retracted, and a spread position in which the spreading elements protrude radially outwards.

By means of such a device, a tubular implant can be pushed onto the introducing head and together with the latter introduced into a vessel. Once the insertion position is reached, the spreading elements can be driven into the spread position by displacement of the locking member mounted on the introducing head. They thereby not only press the implant surrounding the introducing head radially outwardly against the inner wall of the vessel, but also widen out vessel and implant in the area of contact so that a space is created between the introducing head, on the one hand, and the implant and the vessel wall, on the other hand. This space can be used by the operator to fix the implant on the vessel wall from the outside, for example, by performing a circumferential suture or by introducing suitable connecting elements. It is also essential that the two layers of the implant and the vessel wall lying surface-to-surface against each other be tensioned by the extended spreading elements. These spreading elements thus act as abutments so that the two layers to be joined together can be joined by the surgeon in this area lifted off the introducing head, without there being any danger of the layers shifting or deviating during the operation. Provision is made in a preferred embodiment for the introducing head to comprise a releasable holding device for the implant. It is thereby ensured that upon inserting the introducing head and the implant pulled over the latter, the implant is permanently held on the introducing head, but after the implant has been fixed on the vessel, the introducing head can be withdrawn from the operating site without taking the implant along with it by releasing the holding device.

In particular, provision may be made for the holding device to be a flexible bandage, in particular in the form of a thread, which is placed around the implant and holds the implant under tension against the introducing head, with the tension of the bandage being reducible.

Herein it is advantageous for the ends of the bandage to be guided for free displacement along the introducing instrument and along the handle, and, in particular, for them to be guided through the introducing head. The operator is then able to tension the free ends of the bandage at the place at which the device exits from the vessel in order to close the holding device, or to leave the free ends loose in order to release the holding device.

The free ends can, of course, also be connected to an actuating member which, for example, is mounted for displacement along the device.

Herein it is expedient for the introducing head to comprise a recess on its outer surface in the area of the bandage.

This enables the bandage to be fixed along the introducing head, and, in addition, it can thereby be achieved that the bandage does not protrude radially outwardly or only slightly over the circumference of the introducing head.

In particular, this recess can be in the form of a circumferential groove.

The introducing head is preferably in the form of a circular-cylindrical body. It is expedient for the introducing head to be atraumatically rounded-off at its front end opposite the advancing handle, for example, the introducing head may have an approximately spherical-cap-like shape.

The advancing handle can be constructed in the fashion of a catheter, in particular, it can be in the form of a flexible tube which transmits pushing forces.

The spreading elements can be of different design. For example, they can be flexible filler bodies which are expanded outwardly by being filled up with a gas or a liquid, or they can be mechanically extendable spreading elements which, for example, can be transferred from the rest position to the spread position and vice versa via a gear mechanism.

Provision is made in accordance with a preferred embodiment for the spreading elements to be spring elements which are spread radially outwards in the relaxed position.

Herein it is expedient for the spring elements to consist of a superelastic alloy, i.e., of an alloy from the group of the so-called memory alloys which exhibit an extremely elastic deformability, for example, these can be NiTi alloys.

It is advantageous for the spring elements to be arranged in radially outwardly open recesses of the introducing head and to protrude from these recesses in the relaxed state. Thus, in the rest position, these spring elements are driven into the introducing head and do not obstruct insertion of the introducing head and the implant held on the latter into the vessel.

Further provision may be made for the locking member in the rest position to close the recesses on their outer side and thereby push the spring elements into the recesses.

It is particularly advantageous for the locking member to be a tube which is longitudinally displaceable with respect to the introducing head and which closes the recesses in the one position, but releases the recesses in the other position.

Provision may be made for the locking member in the rest position to form a steady continuation of the outer surface of the introducing head so that the tube simultaneously forms a supporting surface for the tubular implant drawn onto the introducing head.

In a preferred embodiment, the spring elements are spring tongues fixed at one side on the introducing head parallel to the longitudinal direction of the introducing head and protruding radially outwardly with their free end in the relaxed state.

These may be thickened and rounded-off atraumatically at their free end in order to prevent damage to the implant and/or the vessel wall.

It is expedient for several such spring elements to be distributed along the circumference of the introducing head so that the tubular implant and the surrounding vessel wall are uniformly expanded in all directions. This enables the surgeon to fix the implant on the vessel along the entire circumference in the same way.

BRIEF DESCRIPTION OF THE DRAWINGS

The following description of preferred embodiments of the invention serves in conjunction with the drawings to explain the invention in greater detail. The drawings show.

DETAILED DESCRIPTION OF THE INVENTION

Figure 1:
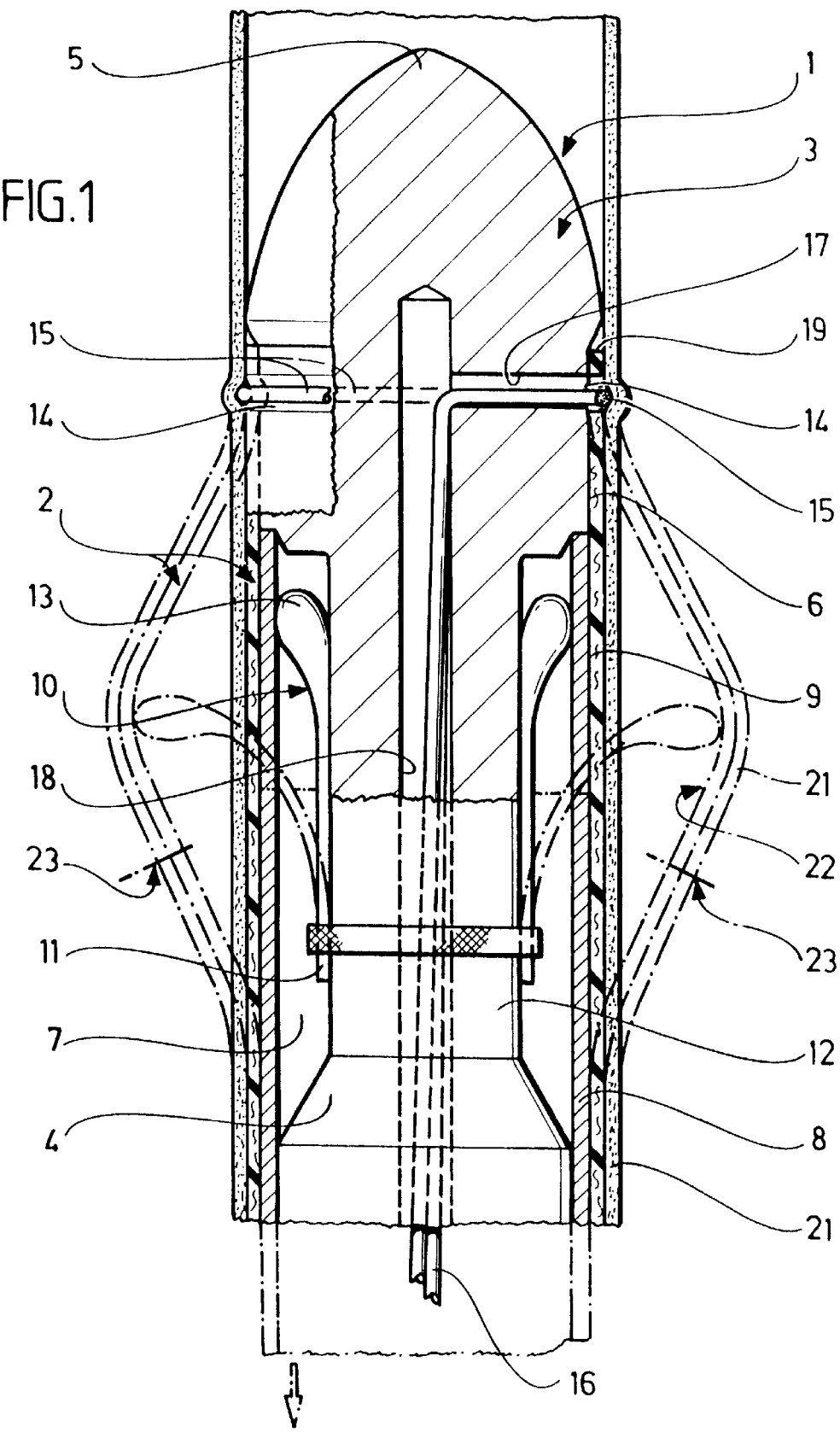
FIG. 1 a longitudinal sectional view through a vessel with an inserted introducing head on which a tubular implant is held, and FIG. 2 a longitudinal sectional view of a vessel section with an expansion and with an inserted introducing head and radially outwardly deformed spreading elements.

The surgical instrument 1 shown in the drawings for introduction of a tubular implant 2 comprises an essentially circular-cylindrical introducing head 3 which is held on a catheter-like, flexible tube 4 which is of such length that the introducing head 3 can be advanced from a place on the body at which the instrument is introduced into a body vessel to the point of application inside the body.

The introducing head 3 is of essentially circular-cylindrical construction and is rounded-off with, for example, approximately the shape of a spherical cap at its end 5 opposite the tube 4. This rounded-off end 5 protrudes slightly in the radial direction beyond the cylindrical outer surface 6 of the introducing head 3 (FIG. 1).

In the circular-cylindrical area of the introducing head 3, the latter comprises a recess 7 similar to a circumferential groove and set back with respect to the outer circumference. The recess 7 is closable by a tube 8 which is mounted for longitudinal displacement on the introducing head 3. In the closed state, the outer surface 9 of the tube 8 always adjoins the outer surface 6 of the introducing head 3 so as to form a common circular-cylindrical circumferential surface of the introducing head 3.

The tube 8 can be displaced from this rest position in which it closes the recess 7 to an open position in which the recess 7 is radially outwardly released. For reasons which will be explained hereinbelow, this position of the tube 8 will be referred to as spread position.

The displacement of the tube 8 can be carried out by suitable transmission means, for example, the tube 8 can extend as far as the end of the tube 4, and it is also possible for the tube 8 to pass over into a push-and-pull element which extends along the tube 4 to the end thereof. This is not shown in greater detail in the drawings.

In the recess 7, at the bottom 12 thereof, a number of spring tongues 10 extending parallel to the longitudinal direction of the introducing head 3 are fixed at an end 11 such that the spring tongues 10 are uniformly distributed along the circumference of the recess 7. The spring tongues 10 consist of an elastic material, in particular, of a superalloy, and are shaped such that in the relaxed state the spring tongues 10 stand with their free ends 13 out of the recess 7 and protrude radially outwardly over the contour of the introducing head (shown in dot-and-dash lines in FIG. 1). The free ends 13 of the spring tongues are of thickened and rounded-off design.

When the tube 8 is located in the retracted, spread position, all spring tongues 10 can relax in the described way and protrude radially outwardly over the introducing head 3. On displacing the tube 8 into the advanced, closed position, the tube 4 forces all spring tongues 10 against their spring force into the interior of the recess 7 so that when the tube 8 is fully advanced, the spring tongues 10 are fully accommodated in the recess 7 (FIG. 1, solid lines).

Immediately adjacent to the rounded-off end 5 of the introducing head 3, the latter comprises in the outer surface 6 an annular groove 14 in which a thread 15 is inserted. The free ends 16 of this thread 15 extend through a radial bore 17 into an axial channel 18 of the introducing head 3, which opens into the interior of the tube 4. The free ends 16 run through this tube 4 to the end of the tube 4 so that by pulling the two free ends 16, the surgeon can at the end of the tube 4 clamp the thread 15 tightly into the annular groove 14, whereas this tension is released again upon releasing the free ends 16.

The described instrument is used in the following way to insert the implant 2:

The tubular implant 2 is first pushed onto the introducing head 3 so that it rests surface-to-surface on the outer surface 6 of the introducing head 3 and on the outer surface 9 of the tube 8 standing in the closed position and with its free edge 19 covers the annular groove 14. In the region of this annular groove 14, the thread 15 is placed around the implant 2, introduced through a cut in the implant 2 into the radial bore 17 and tightened by pulling on the free ends 16 so that the implant 2 is fixed on the introducing head 3.

Figure 2:
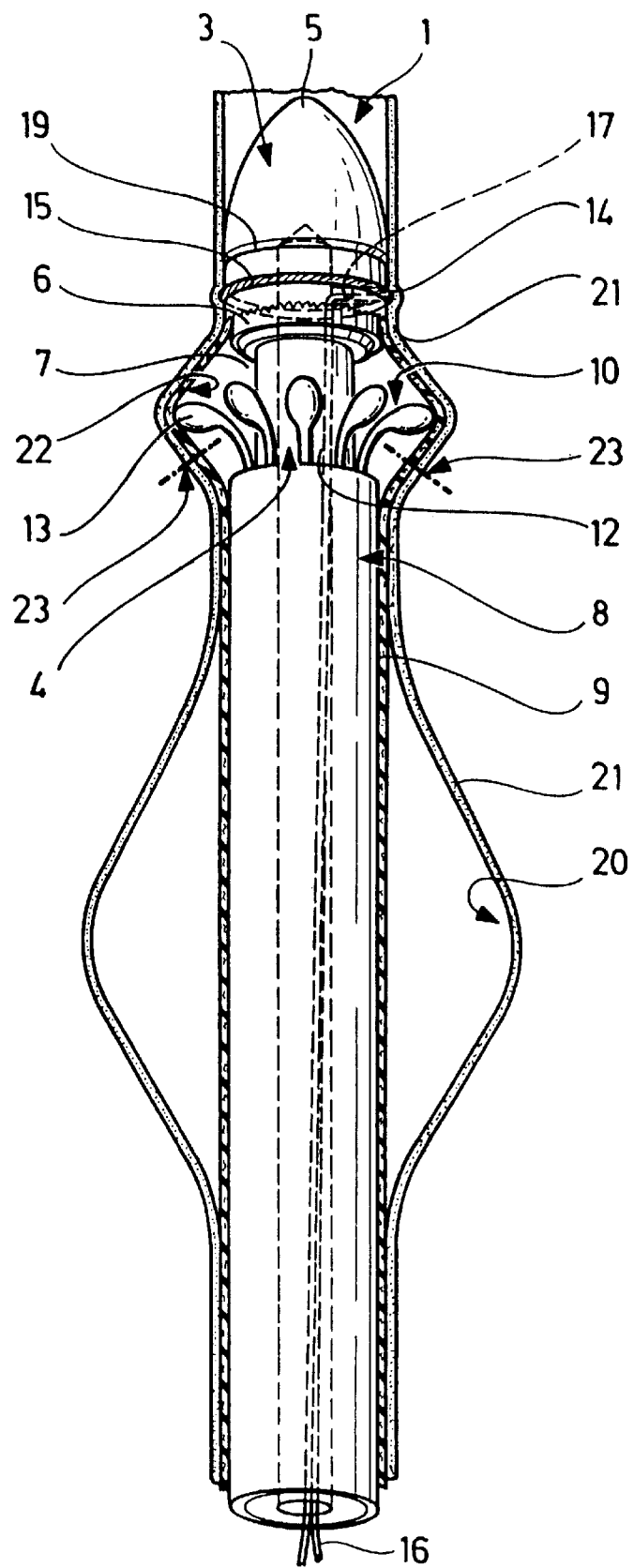

The thus prepared introducing head 3 is pushed through an opening in the vessel into the vessel and advanced therein up to the place at which the implant 2 is to be inserted. The implant 2 is positioned so as to bridge the aneurysm 20 (FIG. 2).

Once this position is reached, the operator pulls the tube 8 back into the spread position and this results in the spring tongues 10 relaxing radially outwardly along the entire circumference of the introducing head 3 and thereby elastically expanding both the implant 2 and the vessel wall 21 (dot-and-dash lines in FIG. 1). They thus raise implant 2 and vessel wall 21 off the outer surface 6 of the introducing head 3 and form an annular space 22 between introducing head 3 and implant/vessel wall. In the region of the annular space 22, they tension both the implant 2 and the vessel wall 21 owing to the elastic expansion and thus enable the surgeon with an instrument, not shown in the drawings, which is brought up to the vessel from the outside, to permanently and tightly join together implant 2 and vessel wall 21, for example, by a circumferential suture or by the insertion of hooks or other attachment means which join together surface-to-surface the two layers of the implant 2, on the one hand, and the vessel wall 21, on the other hand. The connection is indicated by reference numeral 23 in the drawings.

For the connection it is of importance that the implant 2 be fixed in the region of its free edge 19 by the thread 15. In the region behind that, the implant is fixed by resting on the outer side on the tube 8 over quite a large area of its length, the outer diameter of the tube 8 being of such size that the implant 2 is elastically expanded. This fixing of the implant on both sides results in the expansion region, i.e., in the region of the annular space 22, in both the implant and the vessel wall being tensioned by the spring tongues and in this tension not being eliminated again by slipping off. In addition to the creation of the annular space 22, this tension is important for the proper joining of the two layers.

Once the joining of the implant 2 to the vessel wall 21 has been carried out at the end adjacent to the free edge 19, the fixing of the implant 2 on the introducing head 3 can be released. This is carried out by relaxing the free ends 16 of the thread 15 which then no longer clamps the implant 2 in the annular groove 14. By pushing the introducing head forward a short distance in the original push-in direction, the thread 15 comes out of the area of contact of the outer side of the implant 2 and so the introducing head 3 can be pulled back again, the thread 15 then remains on the inner side of the implant 2, which itself is fixed in its position by the connection with the vessel wall 21 and does therefore not follow the rearward displacement of the introducing head 3.

The introducing head 3 is now pulled back only to such an extent that it is positioned on the other side of the aneurysm 20. In this position, the tube 8 is once again moved to the spread position so that the spring tongues 10 are again spread outwards and again form a corresponding annular space in which a connection with the vessel wall 21 can now be made in the same way at the opposite end of the implant 2.

After completion of this connection, the spring tongues 10 are driven in again by pushing forward the tube 8, and the introducing head 3 can then be removed from the vessel again.

As a result of this operation one obtains an implant 2 inserted into the vessel and bridging the aneurysm 20, with the implant 2 being permanently and sealingly connected at both of its ends along its circumference to the surrounding vessel wall 21 so that there is no danger of the implant shifting in the vessel or of the region of the aneurysm 20 undergoing further stress owing to leakages.

What is claimed is:

1. Device for inserting a tubular implant into a vessel, said device comprising:
    an introducing head having an advancing handle and being insertable into said implant;
    radially outwardly movable spreading elements arranged on a circumference of said introducing head;
    a locking member mounted on said introducing head, said locking member being displaceable between a rest position in which said spreading elements are radially retracted, and a spread position in which said spreading elements project radially outwards; and
    a releasable holding device in the form of a flexible bandage adapted to undergo tension when placed around said implant for forcing said implant against said introducing head, the tension of said bandage being reducible.

2. Device as defined in claim 1, wherein said bandage is in the form of thread.

3. Device as defined in claim 1, wherein ends of said bandage are guided for free displacement along said introducing head and along said handle.

4. Device as defined in claim 3, wherein said ends of said bandage are guided through said introducing head.

5. Device as defined in claim 1, wherein said introducing head comprises on its outer surface in the area of said bandage a recess.

6. Device as defined in claim 1, wherein said introducing head is a circular-cylindrical body.

7. Device as defined in claim 1, wherein said introducing head is atraumatically rounded-off at its front end opposite said advancing handle.

8. Device as defined in claim 1, wherein said advancing handle is formed by a flexible tube which transmits pushing forces.

9. Device as defined in claim 1, wherein said spreading elements are spring elements which in the relaxed position are spread radially outwards.

10. Device as defined in claim 9, wherein said spring elements consist of a superelastic alloy.

11. Device as defined in claim 9, wherein said spring elements are arranged in a radially outwardly open recess of said introducing head and in the relaxed state protrude from said recess.

12. Device as defined in claim 11, wherein said locking member in the rest position closes said recess on its outer side and thereby pushes said spring elements into said recess.

13. Device as defined in claim 12, wherein said locking member is a tube which is longitudinally displaceable with respect to said introducing head.

14. Device as defined in claim 13, wherein said locking member in the rest position forms a steady continuation of the outer surface of said introducing head.

15. Device as defined in claim 9, wherein said spring elements are spring tongues fixed at one side on said introducing head parallel to the longitudinal direction of said introducing head and protruding radially outwards at their free end in the relaxed state.

16. Device as defined in claim 15, wherein said spring elements are atraumatically thickened and rounded-off at their free end.

17. Device as defined in claim 15, wherein several such spring elements are distributed along the circumference of said introducing head.

* * * * *